US007973184B2

(12) United States Patent
Haruta et al.

(10) Patent No.: US 7,973,184 B2
(45) Date of Patent: Jul. 5, 2011

(54) METHOD FOR PRODUCING PROPYLENE OXIDE

(75) Inventors: Masatake Haruta, Tokyo (JP); Jiahui Huang, Tokyo (JP); Takashi Takei, Tokyo (JP); Tomoki Akita, Oaska (JP)

(73) Assignees: Tokyo Metropolitan University, Tokyo (JP); National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 12/720,185

(22) Filed: Mar. 9, 2010

(65) Prior Publication Data

US 2010/0234623 A1    Sep. 16, 2010

(30) Foreign Application Priority Data

Mar. 13, 2009 (JP) ................. 2009-061683

(51) Int. Cl.
  *C07D 301/03*    (2006.01)
  *C07D 301/06*    (2006.01)
(52) U.S. Cl. ..................... 549/533; 549/523
(58) Field of Classification Search ........... 549/523, 549/533
  See application file for complete search history.

(56) References Cited

U.S. PATENT DOCUMENTS

| 3,329,481 A | 7/1967 | Young et al. |
| 4,410,501 A | 10/1983 | Taramasso et al. |

FOREIGN PATENT DOCUMENTS

| JP | 8-127550 | 5/1996 |
| JP | 2832336 | 10/1998 |
| JP | 2003-81955 | 3/2003 |

OTHER PUBLICATIONS

Shigeo T. Oyama, et al., "Catalysts & Catalysis", vol. 46, No. 1, 2004, pp. 13-18, Catalysis Society of Japan. (In Japanese with English Abstract).

Masatake Haruta, et al., "Epoxidation of Propylene with Oxygen-Hydrogen Mixtures", Mechanism in Homogeneous and Heterogeneous Expoxidation Catalysis, 2008, chapter 10, pp. 297-313, Elsevier B.V.

Sungsik Lee, et al., "Selective Propene Expoxidation on Immobilized $Au_{6-10}$ Clusters: The Effect of Hydrogen and Water on Activity and Selectivity", Angew. Chem. Int. Ed., 2009, vol. 48, pp. 1467-1471, Wiley-VCH Verlag GmbH & Co. KGaA, Weinheim.

Manuel Ojeda, et al., "Catalytic epoxidation of propene with $H_2O-O_2$ reactants on $Au/TiO_2$", Chem. Commun., 2009, pp. 352-354, The Royal Society of Chemistry.

Jiahui Huang., et al., "Propylene Epoxidation Catalyzed by Gold Clusters Dispersed on Mesoporous TS1", 103rd CATSJ Meeting Abstracts: No. 2 B 09, 2009, vol. 51, No. 2, pp. 171-173.

(Continued)

*Primary Examiner* — Victor Oh
(74) *Attorney, Agent, or Firm* — McDermott Will & Emery LLP (57) ABSTRACT

Disclosed is a method for producing propylene oxide wherein propylene is directly oxidized with oxygen, as required, water and a catalytic amount of hydrogen in a gas phase in the presence of a gold cluster catalyst supported on an alkali-treated titanosilicalite or mesoporous titanosilicate support, which is produced by an alkaline treatment of titanosilicalite or mesoporous titanosilicate with aqueous solution of NaOH, KOH or CsOH.

12 Claims, 1 Drawing Sheet

OTHER PUBLICATIONS

Peng Wu., et al., "Unique *trans*-Selectivity of Ti-MWW in Epoxidation of *cis/trans*-Alkenes with Hydrogen Peroxide", J. Phys. Chem, 2002, vol. 106, pp. 748-753, American Chemical Society.

Shigeo T. Oyama, et al., "Catalysts & Catalysis", vol. 46, No. 1, 2004, pp. 13-18, Catalysts Society of Japan (in Japanese with English Abstract).

Masatake Haruta, et al., "Epoxidation of Propylene with Oxygen-Hydrogen Mixtures", Mechanism in Homogeneous and Heterogeneous Expoxidation Catalysis, 2008, chapter 10, pp. 297-313, Elsevier B.V.

Sungsik Lee, et al., "Selective Propene Expoxidation on Immobilized $Au_{8-10}$ Clusters: The Effect of Hydrogen and Water on Activity and Selectivity", Angew. Chem. Int. Ed., 2009, vol. 48, pp. 1467-1471, Wiley-VCH Verlag GmbH & Co. KGaA, Weinheim.

Manuel Ojeda, et al., "Catalytic epoxidation of propene with $H_2 0-0_2$ reactants on $Au/TiO_2$ ", Chem. Commun., 2009, pp. 362-354, The Royal Society of Chemistry.

Jiahul Huang, et al, "Propylene Epoxidation Catalyzed by Gold Clusters Dispersed on Mesoporous TS1", 103rd CATSJ Meeting Abstracts: No. 2 B 09, 2009, vol. 51, No. 2, pp. 171-173.

Peng Wu., et al., "Unique *trans*-Selectivity of TI-MWW in Epoxidation of *cis/trans*-Alkenes with Hydrogen Peroxide", J. Phys. Chem, 2002, vol. 106, pp. 748-753, American Chemical Society.

METHOD FOR PRODUCING PROPYLENE OXIDE

BACKGROUND OF THE INVENTION

1. Field of the Invention

The present invention relates to a method for producing propylene oxide, in more detail, a method for producing propylene oxide from propylene by a one-step process in gas phase with a gold catalyst and molecular oxygen.

2. Description of the Related Art

Propylene oxide is an important chemical feedstock as an universal intermediate for producing chemicals, for example, polyurethane resins, polyester resins, drugs, additives for cosmetics, heat media, solvents, antifreezing fluids (propylene glycol) or the like, which are used when manufacturing various products such as automobiles, electrical appliances etc. As current main industrial production methods of propylene oxide, there are exemplified a chlorohydrin method and an organic peroxide method. In the chlorohydrin method, propylene chlorohydrin is produced from propylene, chlorine and water, and the propylene chlorohydrin obtained is epoxidized with calcium hydroxide. In the organic peroxide method, propylene is epoxidized with an organic peroxide. It is known that t-butanol, cumyl alcohol or styrene is by-produced in the latter organic peroxide method. In the organic peroxide method, alcohol corresponding to the peroxide used is produced as a by-product; accordingly, there was a problem of a market of the by-products or derivatives thereof, that is, a problem of difficulty in utilizing the by-products due to an unbalance between demand and supply thereof. On the other hand, a large quantity of calcium chloride is by-produced and poisonous chlorinated organic compounds are by-produced in the chlorohydrin method. Therefore, a method for producing propylene oxide without accompanying the production of by-products has been studied. A method where no by-product is resultantly produced by returning cumyl alcohol, that is a by-product in the production method using cumene, to cumene again and reusing it (see JP-A No. 2003-81955) and a method where hydrogen peroxide is used as a peroxide so as to form only water as a by-product to eliminate the disposal of a by-product and no other by-product is produced (see JP-A No. 08-127550) have been recently put into operation. However, the method using hydrogen peroxide has a problem of the cost of hydrogen peroxide and a risk problem due to the use of concentrated hydrogen peroxide. Further, in the method reusing cumyl alcohol that is a by-product, there is a problem that hydrogen is necessary when cumyl alcohol is reduced to cumene.

As a method other than the methods mentioned above, a method where propylene and molecular oxygen are directly reacted in a gas phase in the presence of a catalyst is also well known as a laboratory scale method for producing propylene oxide from propylene (see Shigeo T. Oyama, K. Murata, and M. Haruta, Catalysts & Catalysis, 46 (1), pp. 13 to 18 (2004) and "Mechanisms in Homogeneous and Heterogeneous Epoxidation Catalysis", ed. S. T. Oyama, Elsevir B. V. (2008), pp. 297 to 313). A silver catalyst and a gold catalyst have been extensively studied as a catalyst for the gas phase reaction. Further, it was also reported by the present inventors and others that when propylene is oxidized in the presence of molecular oxygen and hydrogen, propylene oxide can be highly selectively produced when these catalysts are used (see "Mechanisms in Homogeneous and Heterogeneous Epoxidation Catalysis", ed. S. T. Oyama, Elsevir B. V. (2008), pp. 297 to 313). The method is a method where propylene is directly oxidized with a gold titanium-containing oxide catalyst such as an Au/$TiO_2$ catalyst or an Au/Ti—$SiO_2$ catalyst in the presence of a mixed gas of molecular oxygen and hydrogen. Furthermore, it is also known that Au/titanosilicalite (TS-1) is a gold catalyst excellent in catalyst stability.

In a method where propylene oxide is produced from propylene with a catalyst, oxygen and hydrogen as well as a gold catalyst are necessary. On the other hand, there was recently published a paper concerning the formation of propylene oxide at a propylene-oxygen system, a propylene-oxygen-hydrogen system or a propylene-oxygen-water system with a catalyst obtained by depositing gold clusters of 6 to 10 gold atoms on an amorphous alumina support which is formed on a planar substrate, and the formation of propylene oxide was confirmed in this study (see Sungsik Lee et. al, Angew. Chem., Int. Ed., 48, 1467 to 1471 (2009)). However, the conversion rate of propylene and the formation rates of CO and $CO_2$ are unclear since a catalyst is formed into a thin film. It is, therefore, difficult to discuss the practical significance of this paper. On the other hand, a paper concerning the formation of propylene oxide at a propylene-oxygen-hydrogen system or a propylene-oxygen-water system with a $TiO_2$ catalyst, where gold nano-particles having an average particle diameter of 3.5 nm are deposited, was also published (see Manuel Ojeda and Enrique Iglesia, Chem. Commun, 352 to 354 (2009)). However, the conversion rate to propylene oxide in the paper is very small such as 0.02 to 0.06% and the method is far from a practical level.

Thus, it is necessary to use a stoichiometrical amount of hydrogen in conventional methods for producing propylene oxide. However, hydrogen is expensive and has a risk of explosion. Accordingly, if it is possible to produce propylene oxide by the direct oxidation of propylene at a high conversion rate with a smaller amount of hydrogen than a stoichiometrical amount, propylene oxide can be produced inexpensively and safely from propylene.

SUMMARY OF THE INVENTION

Various methods have been studied as a method for producing propylene oxide from propylene till now and some of these have been industrially put into practical use. However, requested is a method for producing propylene oxide inexpensively and safely without the requirement of a safety management, the use of relatively expensive hydrogen or hydrogen peroxide, and the formation of a by-product corresponding to an organic peroxide when the organic peroxide is used.

An object of the present invention is to provide a method for producing propylene oxide at a high selectivity by directly reacting propylene and oxygen in the presence of a catalyst.

As a result of intensive studies and investigation, the present inventors found that propylene oxide can be produced from propylene by a direct oxidation only with oxygen when a particular gold catalyst is used as a catalyst. In addition, the present inventors also found that propylene oxide can be produced with high conversion rate and high selectivity when water is contained in a reaction gas, that is, water is added to a reaction gas, or a reducing gas such as a catalytic amount of hydrogen or CO gas is added to a reaction gas. The present invention was completed based on these findings.

The present invention relates to methods for producing propylene oxide, which are shown below.

(1) A method for producing propylene oxide, wherein propylene is directly oxidized with oxygen in a gas phase in the presence of a gold cluster catalyst supported on an alkali-treated titanosilicalite support or on an alkali-treated mesoporous titanosilicate support.

(2) The method for producing propylene oxide according to the item (1), wherein water is further added to a feed gas comprising propylene and oxygen.

(3) The method for producing propylene oxide according to the item (1) or (2), wherein a catalytic amount of hydrogen gas is further added to a feed gas comprising propylene and oxygen or propylene, oxygen and water.

(4) The method for producing propylene oxide according to any one of the items (1) to (3), the alkali-treated titanosilicalite or mesoporous titanosilicate is the one produced by an alkaline treatment with aqueous solution of NaOH, KOH or CsOH.

(5) The method for producing propylene oxide according to any one of the items (1) to (4), wherein the gold clusters have an average particle diameter of 2 nm or less and an amount of the gold clusters supported on a support is 0.01 to 10% by weight with respect to the weight of the support.

(6) The method for producing propylene oxide according to any one of the items (1) to (5), wherein the gold clusters are supported on the alkali-treated titanosilicalite support or on the alkali-treated mesoporous titanosilicate support by a solid phase grinding method, an impregnation method, a deposition reduction method, a deposition precipitation method or a gas phase grafting method.

(7) The method for producing propylene oxide according to any one of the items (1) to (6), wherein the ratio (volume ratio) of propylene to oxygen is 100:1 to 1:100.

(8) The method for producing propylene oxide according to any one of the items (2) to (6), wherein the ratio (volume ratio) of propylene to oxygen to water is 1 to 100:1 to 100:0.1 to 10.

(9) The method for producing propylene oxide according to any one of the items (3) to (6), wherein the ratio (volume ratio) of propylene to oxygen to hydrogen is 1 to 100:1 to 100:0.1 to 10.

(10) The method for producing propylene oxide according to any one of the items (3) to (6), wherein the ratio (volume ratio) of propylene to oxygen to water to hydrogen is 1 to 100:1 to 100:0.1 to 10:0.1 to 10.

(11) The method for producing propylene oxide according to any one of the items (1) to (10), wherein the reaction temperature is 50 to 300° C. and the space velocity of feed gas is 1,000 to 20,000 $h^{-1} \cdot ml/g$-cat.

ADVANTAGEOUS EFFECT OF THE INVENTION

In the present invention, when a gold cluster catalyst supported on an alkali-treated titanosilicalite support or on an alkali-treated mesoporous titanosilicate support is used as a catalyst, propylene oxide can be produced with high selectivity and, when water and/or hydrogen is added to a feed gas containing propylene and oxygen, a conversion rate of propylene and a selectivity of propylene oxide can be further improved.

DETAILED DESCRIPTION OF THE INVENTION

A method for producing propylene oxide of the present invention will be described below in detail.

In the method for producing propylene oxide of the present invention, it is necessary to use gold clusters supported on an alkali-treated titanosilicalite support or on an alkali-treated mesoporous titanosilicate support as a catalyst.

Both of titanosilicalite and mesoporous titanosilicate, which are used as a support of a gold catalyst in the invention, are known as materials for a support of a catalyst, for example, titanosilicalite is known as TS-1, Ti-MWW or the like and mesoporous titanosilicate as Ti-MCM41, Ti-TUD or the like. The titanosilicalite (hereinafter, abbreviated as TS-1) is shown by, for example, the formula: $xTiO_2(1-x)SiO_2$ (in the formula, x is 0.0005 to 0.04) and the production method thereof is described in, for example, U.S. Pat. Nos. 3,329,481 and 4,410,501. Further, Ti-MWW has the same composition as TS-1 and the production method thereof is described in, for example, Peng Wu and Takashi Tatumi, J. Phys. Chem. B 106, pp. 748 to 753 (2002).

In the present invention, an alkali-treated TS-1 or an alkali-treated Ti-MWW is used as a catalytic support. As an alkali, that is, an alkaline material used in an alkaline treatment of TS-1 and Ti-MWW, there are preferably exemplified hydroxides of alkali metals and alkaline earth metals such as NaOH, KOH, CsOH, Mg (OH)$_2$ and Ba(OH)$_2$. Further, in the treatment, a treatment with an aqueous solution of alkali metal hydroxide such as NaOH, KOH or CsOH is preferred. The treatment may be conducted in such a manner as follows. The TS-1 or Ti-MWW is put into an alkaline aqueous solution followed by stirring at a predetermined temperature for a predetermined time. After that, the alkali aqueous solution is removed by filtration etc. and the alkali-treated TS-1 or Ti-MWW obtained is thoroughly washed with water and dried. A concentration, pH value, and treatment temperature of the alkaline aqueous solution and a treatment time with the alkaline aqueous solution can be arbitrarily chosen. These conditions are usually set as shown below. That is, the pH value of the alkali aqueous solution is 10 to 13, preferably 11 to 12, the treatment temperature is 10 to 80° C., preferably 25 to 50° C. and the treatment time is 0.5 to 10 hours, preferably 1 hour to 4 hours. For example, when TS-1 is treated in an aqueous solution of NaOH or KOH having pH 12 at 30° C. under stirring for about 1 hour to about 4 hours, a mesoporous TS-1 porous body having an average pore diameter of about 5 nm to about 15 nm is formed.

Gold clusters are supported on thus-obtained alkali-treated TS-1 or alkali-treated Ti-MWW. A method for supporting gold clusters may be any one of methods as long as gold clusters can be supported on the alkali-treated TS-1 or alkali-treated Ti-MWW. Examples thereof include a solid phase grinding method, an impregnation method, a deposition reduction method, a deposition precipitation method and a gas phase grafting method. It is preferred that the gold clusters have an average particle diameter of 2 nm or less. The main reason thereof is that when a particle size of the gold clusters becomes 2 nm or less, the catalytic performance of the catalyst can be drastically increased by a change of the electronic structure of the gold clusters owing to a quantum size effect. When an average particle diameter exceeds 2 nm, such a phenomenon that the selectivity to propylene oxide becomes very low takes place. Further, the amount of the gold clusters supported is preferably about 0.01 to 10% by weight. As a supporting method of the gold clusters, a solid phase grinding method is preferred from the viewpoint of facile formation of the gold clusters having an average particle diameter of 2 nm or less on a support. In addition, in the case where mesoporous titanosilicate such as Ti-MCM41 or Ti-TUD is used as a support, the situation is the same as that in the case where TS-1 or Ti-MWW is used as the support.

In the solid phase grinding method, a sublimative gold precursor and a support are mixed in a solid phase with giving friction, followed by performing a reduction treatment or calcination treatment to disperse and fix gold clusters on a support. The amount of the gold precursor may be an amount capable of forming gold clusters having the aforementioned particle diameter and capable of attaining the aforementioned supporting amount. The amount of the gold precursor is usually about $10^{-4}$ to $10^{-1}$ parts by weight relative to 1 part by weight of the support.

As the gold precursor, there are used, for example, $(CH_3)_2Au(CH_3COCHCOCH_3)$, $(CH_3)_2Au(CF_3COCHCOCH_3)$, $(CH_3)_2Au(CF_3COCHCOCF_3)$, $(C_2H_5)_2Au(CH_3COCHCOCH_3$, $(CH_3)_2Au(C_6H_5COCHCOCF_3)$, $ClAuP(CH_3)_3$, $CH_3AuP(CH_3)_3$, and gold complexes represented by the formula 1 or 2:

(1)

wherein $R^1$ represents —$CH_3$ or —$CF_3$, or (2)

wherein $R^2$ represents —$CH_3$ or —$CF_3$ and $R^3$ represents a valeryl group, an isovaleryl group, a pivaloyl group, a tigloyl group, an angeloyl group, a senecioyl group, a phenyl group, a thienyl group or a furyl group.

Further, as a reduction method to metallic gold, there can be exemplified a heat-treating method of a support supporting a gold precursor, which is obtained by grinding at the solid phase as mentioned above, at a temperature of about 50° C. to about 150° C. for about 10 minutes to about 24 hours in an atmosphere of reducing gas such as hydrogen, carbon monoxide or alcohol; and a calcination method where the support is heat-treated in air, for example, at 200 to 400° C. for 1 to 5 hours.

When an impregnation method is used, the processes of the treatment are as follows. The alkali-treated TS-1 or the alkali-treated Ti-MWW was added to an aqueous or organic solvent solution of, for example, tetrachloroauric acid, tetrachloroaurate, gold trichloride, gold cyanide, potassium gold cyanide, diethylamine auric acid trichloride, ethylenediamine gold complex, dimethyl gold β-diketone derivative gold complexes or ethyl gold β-diketone derivative gold complexes, followed by thoroughly stirring. After this, the solvent is evaporated from the mixture, followed by heat-treating in an atmosphere of reducing gas or reducing by calcination at relatively high temperatures.

When a deposition reduction method is used, the processes of the treatment are as follows. The aforementioned alkali-treated TS-1 or the alkali-treated Ti-MWW was added to an aqueous or organic solvent solution of tetrachloroauric acid, tetrachloroaurate, gold trichloride, gold cyanide, potassium gold cyanide, diethylamine auric acid trichloride, ethylenediamine gold complex, dimethyl gold β-diketone derivative gold complexes, or ethyl gold β-diketone derivative gold complexes, followed by adding a solution of a reducing agent such as sodium citrate or sodium boron hydride to reduce and deposit as gold nano-particles on a surface of the alkali-treated TS-1 or Ti-MWW. After this, the precipitate is filtered and then dried to obtain a gold cluster catalyst supported on the alkali-treated TS-1 or alkali-treated Ti-MWW support.

In the case of the deposition precipitation method, the processes of the treatment are as follows. The aforementioned alkali-treated TS-1 or Ti-MWW was added to an aqueous or organic solvent solution of tetrachloroauric acid, tetrachloroaurate, gold trichloride, gold cyanide, potassium gold cyanide, diethylamine auric acid trichloride, ethylenediamine gold complex, dimethyl gold β-diketone derivative gold complexes, or ethyl gold β-diketone derivative gold complexes to deposit and precipitate $Au(OH)_3$ on a surface of the alkali-treated TS-1 or Ti-MWW. After this, the gold hydroxide-deposited alkali-treated TS-1 or Ti-MWW was separated and recovered from a mother liquid by decantation or by centrifuging. After washing thoroughly, the precursor was calcined to obtain a gold cluster catalyst supported on the alkali-treated TS-1 or alkali-treated Ti-MWW support.

In the case of the gas phase grafting method, the processes of the treatment are as follows. A sublimative gold precursor is vaporized in a vacuum line to adsorb on a support under reduced pressure. After this, the gold precursor absorbed on the support surfaces was reduced by calcination and thereby gold clusters are dispersed and fixed on the support (see Japanese Patent No. 2832336). As a sublimative gold precursor, the same gold precursors as those cited in the solid phase grinding method can be used.

In the present invention, the production of propylene oxide is conducted in a gas phase, and a gas containing propylene and oxygen, or propylene, oxygen and water, or a gas where a catalytic amount of hydrogen of 1/10 or less based on the amount of propylene or oxygen is further added to the aforementioned gases may be contacted with the gold cluster catalyst supported on the alkali-treated TS-1 at a temperature of, for example, 50 to 300° C. As an apparatus used at this time, common fixed bed flow-type reactors are generally used when a reaction in a gas phase is conducted. For example, a catalyst is filled into a reaction tube and the reaction tube is heated at a predetermined temperature. Then, a gas containing propylene, oxygen and, as required, further water and/or hydrogen are fed into the reaction tube to contact these feed gases with the catalyst, and the reaction gas is recovered. The reaction pressure is preferably 1 to 100 atmospheres. A diluent gas such as nitrogen, argon, helium or carbon dioxide can be mixed with the reactant gas, as required. The amount of the diluent gas is preferably set usually to 1 to 20 times as much as the volume of propylene from the viewpoint of heat of reaction.

A mixing ratio of propylene and oxygen, that are fed into the reaction tube, is not particularly restricted. However, the ratio of propylene to oxygen (by volume) is usually 1 to 100:100 to 1, preferably 1 to 10:10 to 1. Further, a mixing ratio of propylene and oxygen and water is not particularly restricted too. However, the ratio of propylene to oxygen to water (by volume) is usually 1 to 100:1 to 100:0.1 to 10, preferably 1 to 10:1 to 10:0.1 to 5. Furthermore, a mixing ratio of propylene and oxygen and hydrogen gas and a mixing ratio of propylene and oxygen and water and hydrogen gas, each are preferably set, by volume ratio, to 1 to 100:1 to 100:0.1 to 10 and to 1 to 100:1 to 100:0.1 to 10:0.1 to 10. When water and hydrogen gas are added in such amounts, the conversion rate of propylene and the selectivity to propylene oxide are improved. The amount of the reactant gas to be fed, which further comprises a diluents gas as required, is usually 1,000 to 20,000 $h^{-1}$·ml/g-cat and preferably 2,000 to 8,000 $h^{-1}$·ml/g-cat to a weight of the gold catalyst supported. This is because when a reaction gas is fed in the range described above, formation rates of propylene oxide per time and per catalyst weight reach a maximum.

The amount of the catalyst is not particularly restricted too. When an inner diameter of the reaction tube is 6 to 10 mm, the amount of catalyst used is generally about 0.1 to 1 g. It is preferred practically that the catalyst is used in such an amount as that a space velocity (SV) becomes in a range of about 2,000 to 8,000 $hr^{-1}$·ml/g-cat.

Thus-obtained propylene oxide-containing gas is collected, propylene oxide is then separated from the reaction gas, and the gas not containing propylene oxide after being separated can be reused as a reactant gas, as required.

EXAMPLES

Hereinafter, the present invention will be specifically described with reference to Examples. However, the present invention is not restricted thereto.

Example 1

[Preparation of Support]

50 ml of water in which 5 g of poly(acrylamide-co-diallyldimethylammonium chloride) was dissolved in a concentration of 10% by weight was added under stirring to 144 ml of water in which 36 g of tetrapropyl ammonium hydroxide was dissolved in a concentration of 25% by weight. After continuing stirring for 1 hour, 29 g of tetraethyl orthosilicate and 0.98 g of tetrabutyl orthotitanate were added thereto. After stirring the mixed solution for another 24 hours, a hydrothermal synthesis was performed at 180° C. for 5 days. The resulting solid material was separated, washed, dried at 100° C., and calcined in air at 550° C. for 4 hours to prepare titanosilicalite (TS-1). The resulting TS-1 was suspended in an aqueous potassium hydroxide solution of pH 12 at 30° C., followed by continuing stirring for 1 hour. The TS-1 was separated by a suction filtration, washed with distilled water, dried at 100° C. for half a day, and thereby TS-1-K1 that was obtained by treating TS-1 with potassium hydroxide for 1 hour was obtained.

[Preparation of Gold Cluster-supported Catalyst]

6.6 mg of dimethyl gold acetylacetonate (molecular weight: 326 g/mol) was weighed, followed by grinding with 2 g of the obtained TS-1-K1 for 20 minutes in a mortar. The mixed powder was filled into a U-shaped quartz reaction tube and a nitrogen gas containing 10% by volume of hydrogen was passed through in the tube. Thereafter, heating at 150° C. was performed for 2 hours for a reduction treatment, and thereby, 0.2% by weight Au/TS-1-K1 where 0.2% by weight of gold cluster was supported on the potassium hydroxide-treated TS-1-K1 was obtained. The diameters of gold particles for thus-obtained gold clusters supported on potassium hydroxide-treated TS-1-K1 were measured according to a method shown below.

[Measurement of Diameter of Gold Particle]

Figure 1:
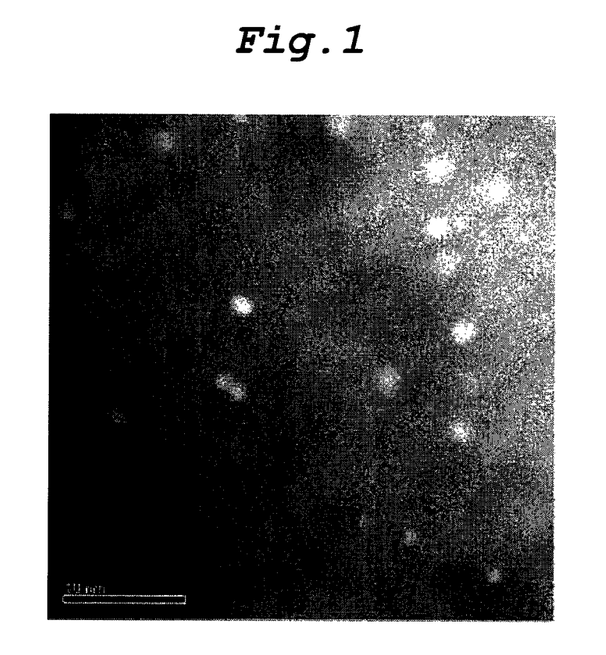
FIG. 1 is a HAADF-STEM (High Angle Annular Dark Field-Scanning Transmission Electron Microscopy) image of a gold cluster catalyst supported on a potassium hydroxide-treated TS-1 support (0.2% by weight Au/TS-1-K1) obtained in Example 1.
Figure 2:
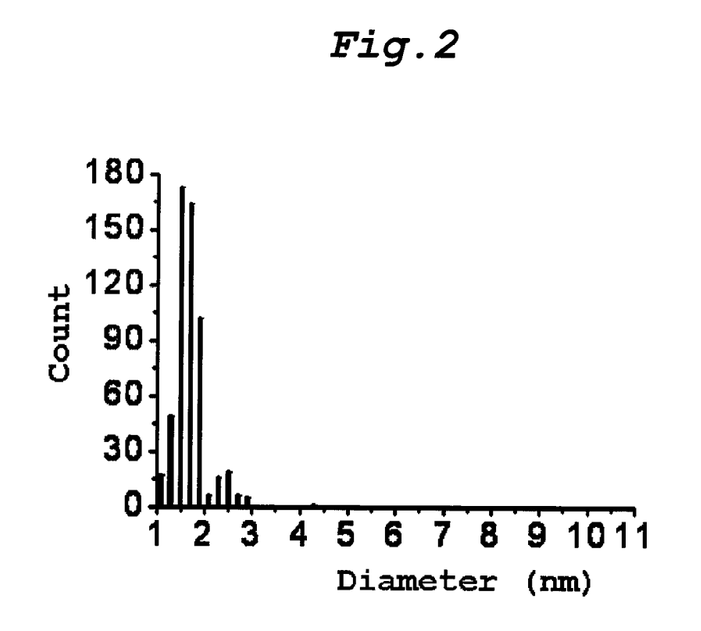
FIG. 2 is a graph showing a particle size distribution of a gold cluster catalyst supported on a potassium hydroxide-treated TS-1 (0.2% by weight Au/TS-1-K1) obtained in Example 1.

A part of the resulting powder sample was suspended in distilled water, followed by subjecting to an ultrasonic wave for 10 minutes to accelerate dispersion of a flocculated powder sample. The suspension was thoroughly stirred with a narrow glass rod and one drop thereof was placed on a carbon-deposited copper grid which is used for the observation by a transmission electron microscope (TEM). Then, the grid was stored in a desiccator for half a day to dry. The sample obtained was observed with an ordinary TEM, but existence of gold could not be clearly confirmed. Therefore, an observation of the sample was performed by a HAADF-STEM (High Angle Annular Dark Field-Scanning TEM). The use of the HAADF-STEM is effective to observe fine gold clusters because the contrast increases in proportion to the square of an atomic number. FIG. 1 shows an HAADF-STEM image. Further, diameters of individual gold particles in the HAADF-STEM images at arbitrary 10 points or more were measured to investigate a distribution of particle size. Results are shown in FIG. 2. From FIG. 2, it was found that about 90% or more of the gold particles have a diameter of 2.0 nm or less and an average particle diameter thereof is 1.5 nm (the number of atoms: about 55).

[Oxidation of Propylene with Oxygen]

0.3 g of the resulting 0.2% by weight Au/TS-1-K1 was weighted and filled into a U-shaped quartz reaction tube and a reactant gas consisting of $C_3H_6/O_2$/Ar (volume ratio)=1/1/7 was flowed in the tube at a flow rate of 20 ml/min. An hourly space velocity was set at 4,000 $h^{-1}$·ml/g-cat. When the temperature of the catalytic layer was set at 200° C., the conversion rate of propylene reached 1.0 to 2.0% and then gradually decreased with time on stream. However, after 2 hours, almost no change of the conversion rate was observed, that is, the reaction reached a steady state. In this state, the conversion rate of propylene and the selectivity to each of propylene oxide (PO), acrolein (AC) and $CO_2$ were investigated by a gas chromatography. Results are shown in Table 1.

Comparative Example 1

A 0.2% by weight Au/TS-1 was prepared by using, as a support, the TS-1 which was a support produced in Example 1 before treatment with potassium hydroxide, and by allowing 0.2% by weight of gold clusters to support thereon by the same manner as Example 1.

The oxidation of propylene was conducted under the same conditions as Example 1 by use of the gold cluster catalyst supported on the TS-1 support and the conversion rate of propylene and the selectivity to each of propylene oxide (PO), acrolein (AC) and $CO_2$ in this oxidation treatment were investigated. Results are shown in Table 1.

Comparative Example 2

A 1.0% by weight Au/C catalyst was prepared by allowing 1.0% by weight of gold cluster to support on a nonporous carbon according to the same solid phase-grinding method (SG) as Example 1 except that the calcination at 200° C. in air was conducted in place of the hydrogen reduction at 150° C.

The oxidation of propylene was conducted under the same condition as Example 1 by use of the gold cluster catalyst supported on the nonporous carbon support and the conversion rate of propylene and the selectivity to each of propylene oxide (PO), acrolein (AC) and $CO_2$ in this oxidation treatment were investigated. Results are shown in Table 1.

Comparative Example 3

A 1.0% by weight Au/γ-$Al_2O_3$ catalyst was prepared by allowing 1.0% by weight of gold cluster to support on $\gamma$-$Al_2O_3$ according to the same solid phase-grinding method (SG) as Example 1 except that the calcination at 300° C. in air was conducted in place of the hydrogen reduction at 150° C.

The oxidation of propylene was conducted under the same condition as Example 1 by use of the gold cluster catalyst supported on the $\gamma$-$Al_2O_3$ support and the conversion rate of propylene and the selectivity to each of propylene oxide (PO), acrolein (AC) and $CO_2$ in this oxidation treatment were investigated. Results are shown in Table 1.

Comparative Example 4

A 0.2% by weight Au/$Al_2O_3$ catalyst was prepared by allowing 0.2% by weight of gold cluster to support on $Al_2O_3$ according to the same solid phase-grinding (SG) method as Example 1.

The oxidation of propylene was conducted under the same condition as Example 1 by use of the gold cluster catalyst supported on $Al_2O_3$ and the conversion rate of propylene and the selectivity to each of propylene oxide (PO), acrolein (AC) and $CO_2$ in this oxidation treatment were investigated. Results are shown in Table 1.

Comparative Example 5

A 1.0% by weight Au/$TiO_2$ catalyst was prepared by the way that gold hydroxide was precipitated and deposited on a $TiO_2$ support by a deposition precipitation method (DP) at a condition of 70° C., pH 7.0 adjusted with an aqueous KOH solution, and stirring for 1 hour and then the precipitate was separated by filtration, washed with water, dried at 100° C., and calcined at 300° C. in air to deposit 1.0% by weight of gold cluster on the $TiO_2$ support.

The oxidation of propylene was conducted under the same condition as Example 1 by use of the gold cluster catalyst supported on the $TiO_2$ support and the conversion rate of propylene and the selectivity to each of propylene oxide (PO), acrolein (AC) and $CO_2$ in this oxidation treatment were investigated. Results are shown in Table 1.

TABLE 1

| | Support | Supporting amount of gold (%) | Method of supporting gold | Average particle diameter of gold (nm) | Convertion rate (%) | Selectivity (%) | | |
|---|---|---|---|---|---|---|---|---|
| | | | | | | PO | AC | $CO_2$ |
| Example 1 | TS-1-K1 | 0.2 | SG | 1.8 | 0.33 | 11.8 | 31.7 | 56.5 |
| Comparative Example 1 | TS-1 | 0.2 | SG | 4.6 | 0.05 | 0.0 | 42.7 | 57.3 |
| Comparative Example 2 | Carbon | 1.0 | SG | 1.9 | 0.33 | 0.0 | 45.2 | 54.8 |
| Comparative Example 3 | $\gamma$-$Al_2O_3$ | 1.0 | SG | 2.6 | 0.14 | 0.0 | 23.7 | 59.4 |
| Comparative Example 4 | $Al_2O_3$ | 0.2 | SG | <2.0 | 0.07 | 0.0 | 50.2 | 49.8 |
| Comparative Example 5 | $TiO_2$ | 1.0 | DP | 2.9 | 0.0 | 0.0 | 0.0 | 0.0 |

(Addition Effect of Water)

Example 2

Propylene was oxidized in the same manner as Example 1 except that a reaction gas was bubbled in water at 0° C. to add moisture up to the saturated water vapor pressure and the conversion rate of propylene and the selectivity to each of propylene oxide (PO), acrolein (AC) and $CO_2$ in this oxidation treatment were investigated. Results are shown in Table 2.

Comparative Examples 6 to 10

Propylene was oxidized in the same manner as each of Comparative examples 1 to 5 except that a reaction gas was bubbled in water at 0° C. to add moisture up to the saturated water vapor pressure and the conversion rate of propylene and the selectivity to each of propylene oxide (PO), acrolein (AC) and $CO_2$ in these oxidation treatments were investigated. Results are shown in Table 2.

TABLE 2

| | Support | Supporting amount of gold (%) | Method of supporting gold | Average particle diameter of gold (nm) | Conversion rate (%) | Selectivity (%) | | |
|---|---|---|---|---|---|---|---|---|
| | | | | | | PO | AC | $CO_2$ |
| Example 2 | TS-1-K1 | 0.2 | SG | 1.8 | 0.88 | 51.5 | 12.3 | 36.3 |
| Comparative Example 6 | TS-1 | 0.2 | SG | 4.6 | 0.07 | 0.0 | 33.9 | 66.1 |

TABLE 2-continued

| | Support | Supporting amount of gold (%) | Method of supporting gold | Average particle diameter of gold (nm) | Convertion rate (%) | Selectivity (%) | | |
|---|---|---|---|---|---|---|---|---|
| | | | | | | PO | AC | $CO_2$ |
| Comparative Example 7 | Carbon | 1.0 | SG | 1.9 | 0.48 | 0.0 | 40.5 | 59.5 |
| Comparative Example 8 | $\gamma$-$Al_2O_3$ | 1.0 | SG | 2.6 | 0.15 | 0.0 | 41.3 | 43.6 |
| Comparative Example 9 | $Al_2O_3$ | 0.2 | SG | <2.0 | 0.15 | 0.0 | 53.9 | 46.1 |
| Comparative Example 10 | $TiO_2$ | 1.0 | DP | 2.9 | 0.03 | 0.0 | 0.0 | 100 |

As is obvious from Tables 1 and 2, in the case where supports other than an alkali-treated TS-1 were used, the selectivity to propylene oxide was zero, that is, propylene oxide was not formed in all cases. In addition, it is found that propylene oxide was formed only when an alkali-treated TS-1 was used as a support, and when water was further added in the reaction gas, the rate of conversion of propylene was improved and the selectivity to propylene oxide became remarkably high. Further, it is found from comparative examples 1 and 6 that in the case where the gold catalyst supported on TS-1 which is not alkali-treated is used, when water is added, the formation of acrolein is inhibited and, by contrast, the formation of $CO_2$ was accelerated. However, the addition of water to the reaction gas had no effect on the formation of propylene oxide.

That is, only when a catalyst in which gold clusters having a diameter of 2 nm or less were supported on the alkali-treated TS-1 is used as a catalyst, propylene oxide is formed by molecular oxygen alone and when water is coexisted in a reaction gas, the conversion rate of propylene and the selectivity to propylene oxide are improved.

(Influence of Alkali-treatment Time)

Examples 11 to 13

[Preparations of Supports TS-1-K2 to TS-1-K4]

0.2% by weight Au/TS-1-K2, 0.2% by weight Au/TS-1-K3 and 0.2% by weight Au/TS-1-K4, which are respectively obtained by treating 0.2% by weight Au/TS-1 with potassium hydroxide for 2 hours, 3 hours or 4 hours, were prepared in the same manner as Example 1 except that the stirring time in the aqueous potassium hydroxide solution was changed from 1 hour to 2 hours, 3 hours and 4 hours.

[Oxidation Reaction of Propylene with Oxygen and Water]

Propylene was oxidized in the same manner as Example 2 except that 0.2% by weight Au/TS-1-K2, 0.2% by weight Au/Ts-1-K3 or 0.2% by weight Au/TS-1-K4 was used in place of 0.2% by weight Au/TS-1-K1, and the conversion rate of propylene and the selectivity to each of propylene oxide (PO), acrolein (AC) and $CO_2$ in these oxidation treatments were investigated. Results are shown in Table 3. For the purpose of reference, the results in Example 2 and Comparative example 6 are also shown in Table 3 (two significant figures).

TABLE 3

| Catalyst | | Convertion rate | Selectivity (%) | | |
|---|---|---|---|---|---|
| | (0.2 wt % Au) | (%) | PO | AC | $CO_2$ |
| Example 2 | Au/TS-1-K1 | 0.88 | 52 | 12 | 36 |
| Example 11 | Au/TS-1-K2 | 0.89 | 40 | 8.0 | 49 |
| Example 12 | Au/TS-1-K3 | 0.74 | 41 | 10 | 43 |
| Example 13 | Au/TS-1-K4 | 0.76 | 31 | 9.0 | 56 |

TABLE 3-continued

| Catalyst | | Convertion rate | Selectivity (%) | | |
|---|---|---|---|---|---|
| | (0.2 wt % Au) | (%) | PO | AC | $CO_2$ |
| Comparative Example 6 | Au/TS-1 | 0.07 | 0.0 | 34 | 66. |

From Table 3, the selectivity to propylene oxide is high in all of Examples 2, 11, 12 and 13. Accordingly, it is found from these examples that the treatment time of TS-1 with potassium hydroxide may be any one of the treatment times, that is, the treatment time is not particularly restricted in the present invention. However, from examples of Examples 2, 11, 12 and 13, both of the conversion rate of propylene oxide and the selectivity to propylene oxide tend to decrease as a treatment time with potassium hydroxide is extended from 1 hour to 4 hours; accordingly, it is preferred that the alkali treatment time is set at 1 hour in these examples.

(Influence of Particle Diameter of Gold Cluster)

Examples 14 and 15

[Preparation of Catalyst]

0.2% by weight Au/TS-1-K1 (200° C.) and 0.2% by weight Au/TS-1-K1 (300° C.) were prepared in the same manner as Example 1 except that the calcination was conducted at 200° C. or 300° C. in place of reduction at 150° C.

[Oxidation of Propylene with Oxygen]

Propylene was oxidized in the same manner as Example 1 except that the 0.2% by weight Au/TS-1-K1 (200° C.) or 0.2% by weight Au/TS-1-K1 (300° C.) was used in place of the 0.2% by weight Au/TS-1-K1, and the conversion rate of propylene and the selectivity to each of propylene oxide (PO), acrolein (AC) and $CO_2$ in this oxidation treatment in these oxidation treatments were investigated. Results are shown in Table 4. For the purpose of reference, the results in Example 1 are also shown in Table 4.

Comparative Examples 11 and 12

[Preparation of Catalyst]

0.2% by weight Au/TS-1-K1 (400° C.) and 0.2% by weight Au/TS-1-K1 (500° C.) were prepared in the same manner as Example 1 except that in place of reduction at 150° C., calcination was performed at 400° C. or 500° C.

[Oxidation of Propylene with Oxygen]

Propylene was oxidized in the same manner as Example 1 except that the 0.2% by weight Au/TS-1-K1 (400° C.) or 0.2% by weight Au/TS-1-K1 (500° C.) was used in place of the 0.2% by weight Au/TS-1-K1, and the conversion rate of propylene and the selectivity to each of propylene oxide (PO), acrolein (AC) and $CO_2$ in these oxidation treatments were investigated. Results are shown in Table 4.

In addition, when the calcination temperature is elevated, an average particle diameter of gold clusters to be formed becomes larger. In the gold cluster catalysts produced under the aforementioned conditions, an average particle diameter of Au/TS-1-K1 (200° C.) is 2.0 nm or less, an average particle diameter of Au/TS-1-K1 (300° C.) is 2.0 nm, an average particle diameter of Au/TS-1-K1 (400° C.) is 3.5 nm and an average particle diameter of Au/TS-1-K1 (500° C.) is 3.5 nm or more. Further, an average particle diameter of Au/TS-1-K1 is 1.5 nm as described in Example 1.

3.5 nm and there is no gold cluster of 2 nm or smaller, propylene oxide is not formed even when water is added.

Influence of alkali used in the treatment of TS-1

Examples 18 and 19

[Preparation of Catalyst]

A TS-1-Na1 obtained by treating TS-1 for 1 hour with sodium hydroxide and a TS-1-Cs1 obtained by treating TS-1 for 1 hour with cesium hydroxide were respectively prepared

TABLE 4

| Catalyst (0.2 wt % Au) | | Average particle diameter (nm) | Convertion rate (%) | Selectivity (%) | | |
|---|---|---|---|---|---|---|
| | | | | PO | AC | $CO_2$ |
| Example 1 | Au/TS-1-K1 | 1.5 | 0.33 | 11.8 | 31.7 | 56.5 |
| Example 14 | Au/TS-1-K1 (200° C.) | — | 0.34 | 16.1 | 35.5 | 48.4 |
| Example 15 | Au/TS-1-K1 (300° C.) | 2.0 | 0.41 | 15.6 | 32.7 | 51.7 |
| Comparative Example 11 | Au/TS-1-K1 (400° C.) | 3.5 | 0.09 | 0.0 | 50.5 | 49.5 |
| Comparative Example 12 | Au/TS-1-K1 (500° C.) | — | 0.06 | 0.0 | 49.7 | 50.3 |

Examples 16 and 17, Comparative Examples 13 and 14

Propylene was oxidized in the same manner as each of Examples 14 and 15 and Comparative examples 11 and 12 except that the reaction gas was bubbled in water at 0° C. to add moisture up to a saturated vapor pressure, and the conversion rate of propylene and the selectivity to each of propylene oxide (PO), acrolein (AC) and $CO_2$ in these oxidation treatments were investigated. Results are shown in Table 5. For the purpose of reference, the results in Example 2 are also shown in Table 5.

in the same manner as Example 1 except that sodium hydroxide or cesium hydroxide was used in place of potassium hydroxide.

Thus-obtained TS-1-Na1 and TS-1-Cs1 were used in the same manner as Example 1 to prepare the 0.2% by weight Au/TS-1-Na1 and the 0.2% by weight Au/TS-1-Cs1.

[Oxidation of Propylene with Oxygen and Water]

Propylene was oxidized in the same manner as Example 2 except that the 0.2% by weight Au/TS-1-Na1 or 0.2% by weight Au/TS-1-Cs1 was used in place of 0.2% by weight Au/TS-1-K1, and the conversion rate of propylene and the selectivity of each of propylene oxide (PO), acrolein (AC)

TABLE 5

| Catalyst (0.2 wt % Au) | | Average particle diameter (nm) | Convertion rate (%) | Selectivity (%) | | |
|---|---|---|---|---|---|---|
| | | | | PO | AC | $CO_2$ |
| Example 2 | Au/TS-1-K1 | 1.5 | 0.88 | 51.5 | 12.3 | 36.3 |
| Example 16 | Au/TS-1-K1 (200° C.) | — | 0.93 | 47.6 | 11.5 | 40.8 |
| Example 17 | Au/TS-1-K1 (300° C.) | 2.0 | 0.82 | 50.5 | 10.6 | 38.9 |
| Comparative Example 13 | Au/TS-1-K1 (400° C.) | 3.5 | 0.14 | 34.6 | 19.2 | 46.2 |
| Comparative Example 14 | Au/TS-1-K1 (500° C.) | — | 0.02 | 0.0 | 0.0 | 100 |

It is found from Tables 4 and 5 that when the average particle diameter of gold clusters exceeds 2 nm, propylene oxide is not formed in the case where water is not added and, when the average particle diameter of gold clusters exceeds and $CO_2$ in these oxidation treatments were investigated. Results are shown in Table 6. For the purpose of reference, the results in Example 2 are also shown in Table 6 (two significant figures).

TABLE 6

| Catalyst | Convertion rate | Selectivity (%) | | |
|---|---|---|---|---|
| (0.2 wt % Au) | (%) | PO | AC | $CO_2$ |
| Example 2 | Au/TS-1-K1 | 0.88 | 52 | 12 | 36 |
| Example 18 | Au/TS-1-Na1 | 0.85 | 40 | 14 | 46 |
| Example 19 | Au/TS-1-Cs1 | 0.80 | 38 | 15 | 47 |

It is found from Table 6 that propylene oxide can be obtained at a high conversion rate and a high selectivity even when a kind of alkali is varied. Further, it is also found from Table 6 that the TS-1 treated with potassium hydroxide is preferred among these.

Influence of Method for Supporting Gold

Examples 20 and 21

TS-1-K1 and TS-1-Na1 treated with an alkali (potassium hydroxide or sodium hydroxide) for 1 hour, that support 12% by weight of Au clusters by the deposition precipitation method (DP), were prepared. Propylene was oxidized therewith in the same manner as Example 2, and the conversion rate of propylene and the selectivity to each of propylene oxide (PO), acrolein (AC) and $CO_2$ in these oxidation treatments were investigated. Results are shown in Table 7.

TABLE 7

| Catalyst | Convertion rate | Selectivity (%) | | |
|---|---|---|---|---|
| (12 wt % Au) | (%) | PO | AC | $CO_2$ |
| Example 20 | Au/TS-1-K1 (DP) | 0.46 | 57 | 7.0 | 36 |
| Example 21 | Au/TS-1-Na1 (DP) | 0.54 | 39 | 0.0 | 61 |

It is found from Table 7 that the same advantage as the solid phase grinding method can be obtained even in the case where the deposition precipitation method is used. From this, it is found that an advantage of the present invention can be obtained as long as the TS-1 is treated with an alkali and does not depend on a method for producing a catalyst.

Addition Effect of Catalytic Amount of Hydrogen

Example 22

Propylene was oxidized in the same manner as Example 1 except that 1% by volume of hydrogen was added into the reaction gas, and the conversion rate of propylene and the selectivity to each of propylene oxide (PO), acrolein (AC) and $CO_2$ in this oxidation treatment were investigated. Results at the time when the 0.2% by weight Au/TS-1-K1 was used as the gold catalyst are shown in Table 8.

TABLE 8

| | $C_3H_6/O_2/H_2/Ar = 10/10/1/79$ | | | |
|---|---|---|---|---|
| Reaction | Convertion | Selectivity (%) | | |
| temperature | rate (%) $C_3H_6$ | PO | AC | $CO_2$ |
| 200° C. | 2.3 | 70 | 6.0 | 24 |
| 180° C. | 2.3 | 68 | 0.0 | 30 |
| 160° C. | 2.0 | 83 | 0.0 | 17 |
| 140° C. | 1.6 | 92 | 0.0 | 8.0 |

Example 23

Propylene was oxidized in the same manner as Example 2 except that 1% by volume of hydrogen was added into a reaction gas, and the rate of conversion of propylene and the selectivity to each of propylene oxide (PO), acrolein (AC) and $CO_2$ in this oxidation treatment were investigated. Results at the time when the 0.2% by weight Au/TS-1-K1 was used as the gold catalyst are shown in Table 9.

TABLE 9

| | $C_3H_6/O_2/H_2O/H_2/Ar = 10/10/2/1/77$ | | | |
|---|---|---|---|---|
| Reaction | Convertion | Selectivity (%) | | |
| temperature | rate (%) $C_3H_6$ | PO | AC | $CO_2$ |
| 200° C. | 2.3 | 59 | 8.0 | 27 |
| 180° C. | 1.9 | 77 | 0.0 | 20 |
| 160° C. | 1.5 | 88 | 0.0 | 12 |
| 140° C. | 1.3 | 94 | 0.0 | 6 |

As is obvious from Table 8, when 1% by volume of hydrogen was added, the conversion rate of propylene and the selectivity to propylene oxide both were remarkably improved even when propylene and oxygen are reacted. Further, as is obvious from Table 9, when 1% by volume of hydrogen was added, the conversion rate of propylene and the selectivity to propylene oxide both were remarkably improved even when propylene and oxygen are reacted in the presence of water. From the facts mentioned above, it is found that the addition of a catalytic amount of hydrogen is effective.

Propylene oxide produced according to a production method of the present invention is widely used as an intermediate for the production of polyurethane resins, polyester resins, drugs, additives for cosmetics, heat media, solvents, antifreezing fluids (propylene glycol) or the like.

What is claimed is:

1. A method for producing propylene oxide, wherein propylene is directly oxidized with oxygen in a gas phase in the presence of a gold cluster catalyst supported on an aqueous-alkali-treated titanosilicalite support or on an aqueous-alkali-treated mesoporous titanosilicate support and wherein the gold clusters have an average particle diameter of 2 nm or less.

2. The method for producing propylene oxide according to claim 1, wherein water is further added to a feed gas comprising propylene and oxygen.

3. The method for producing propylene oxide according to claim 1, wherein a catalytic amount of hydrogen gas is further added to a feed gas comprising propylene and oxygen.

4. The method for producing propylene oxide according to claim 2, wherein a catalytic amount of hydrogen gas is further added to a feed gas comprising propylene, oxygen and water.

5. The method for producing propylene oxide according to claim 1, wherein the aqueous-alkali-treated titanosilicalite or mesoporous titanosilicate is produced by an alkaline treatment with an aqueous solution of NaOH, KOH or CsOH.

6. The method for producing propylene oxide according to claim 1, wherein an amount of the gold clusters supported on the support is 0.01 to 10% by weight with respect to the weight of the support.

7. The method for producing propylene oxide according to claim 1, wherein gold clusters are supported on the aqueous-alkali-treated titanosilicalite support or on the aqueous-alkali-treated mesoporous titanosilicate support by a solid phase grinding method, an impregnation method, a deposition reduction method, a deposition precipitation method or a gas phase grafting method.

8. The method for producing propylene oxide according to claim 1, wherein the ratio (volume ratio) of propylene to oxygen is 100:1 to 1:100.

9. The method for producing propylene oxide according to claim 2, wherein the ratio (volume ratio) of propylene to oxygen to water is 1 to 100:1 to 100:0.1 to 10.

10. The method for producing propylene oxide according to claim 3, wherein the ratio (volume ratio) of propylene to oxygen to hydrogen is 1 to 100:1 to 100:0.1 to 10.

11. The method for producing propylene oxide according to claim 4, wherein the ratio (volume ratio) of propylene to oxygen to water to hydrogen is 1 to 100:1 to 100:0.1 to 10:0.1 to 10.

12. The method for producing propylene oxide according to claim 1, wherein the reaction temperature is 50 to 300° C., and the space velocity of the feed gas is 1,000 to 20,000 $h^{-1}$ ml/g-cat.

* * * * *